US007651720B2

(12) United States Patent
Nakajima et al.

(10) Patent No.: US 7,651,720 B2
(45) Date of Patent: Jan. 26, 2010

(54) EPA AND/OR DHA-CONTAINING ACIDIC MILKS

(75) Inventors: Shuji Nakajima, Tokyo (JP); Yoko Yamagishi, Tokyo (JP); Kazuhiko Hata, Hachioji (JP); Jun Okano, Hachioji (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 265 days.

(21) Appl. No.: 10/416,019

(22) PCT Filed: Nov. 12, 2001

(86) PCT No.: PCT/JP01/09879

§ 371 (c)(1),
(2), (4) Date: Oct. 14, 2003

(87) PCT Pub. No.: WO02/37976

PCT Pub. Date: May 16, 2002

(65) Prior Publication Data

US 2004/0131727 A1 Jul. 8, 2004

(30) Foreign Application Priority Data

Nov. 13, 2000 (JP) ............................. 2000-344863

(51) Int. Cl.
A23L 2/38 (2006.01)
(52) U.S. Cl. .................... 426/598; 426/34; 426/44; 426/626
(58) Field of Classification Search ............... 426/34, 426/36, 38, 39, 43, 61, 582, 583, 585, 634, 426/321, 598, 44
See application file for complete search history.

(56) References Cited

U.S. PATENT DOCUMENTS

| | | | | |
|---|---|---|---|---|
| 3,937,843 | A * | 2/1976 | Osaka et al. | 426/46 |
| 4,554,107 | A * | 11/1985 | Takao | 554/212 |
| 4,775,749 | A * | 10/1988 | Hijiya et al. | 536/103 |
| 4,794,017 | A * | 12/1988 | Yajima | 426/634 |
| 4,913,921 | A * | 4/1990 | Schroeder et al. | 426/321 |
| 5,962,062 | A * | 10/1999 | Carrie et al. | 426/585 |
| 5,976,606 | A * | 11/1999 | Koga et al. | 426/634 |
| 6,020,020 | A * | 2/2000 | Cain et al. | 426/601 |
| 6,025,008 | A * | 2/2000 | Akahoshi et al. | 426/583 |
| 6,194,379 | B1 * | 2/2001 | McEwen et al. | 514/2 |
| 6,313,167 | B1 * | 11/2001 | Nakajima et al. | 514/546 |

FOREIGN PATENT DOCUMENTS

| | | |
|---|---|---|
| EP | 0 659 347 A | 6/1995 |
| EP | 0 705 539 A | 4/1996 |
| EP | 0 809 939 A | 12/1997 |
| EP | 0 956 779 A | 11/1999 |
| EP | 0 999 259 A | 5/2000 |
| JP | 60-160840 | 8/1985 |
| JP | 61021048 A * | 1/1986 |
| JP | 61231958 A * | 10/1986 |
| JP | 63216435 A * | 9/1988 |
| JP | 6-90662 | 4/1994 |
| JP | 06090662 A * | 4/1994 |
| JP | 07107907 A * | 4/1995 |
| JP | 7-255406 | 10/1995 |
| JP | 07-255406 | 10/1995 |
| JP | 07255406 A * | 10/1995 |
| JP | 08089167 A * | 4/1996 |
| JP | 8-308521 | 11/1996 |
| JP | 08-308521 | 11/1996 |
| JP | 10146167 A * | 6/1998 |
| JP | 10-201417 | 8/1998 |
| JP | 10-237480 | 9/1998 |
| JP | 10237480 A * | 9/1998 |
| JP | 2002204656 A * | 7/2002 |
| WO | WO 96/37113 | 11/1996 |
| WO | WO 9857628 A1 * | 12/1998 |

* cited by examiner

*Primary Examiner*—Keith D Hendricks
*Assistant Examiner*—Jyoti Chawla
(74) *Attorney, Agent, or Firm*—Westerman, Hattori, Daniels & Adrian, LLP

(57) ABSTRACT

The invention provides dairy products containing fish-oil-originated EPA and/or DHA and having oxidation and emulsification stability. In particular, acidified milk containing EPA and/or DHA is provided which has oxidation and emulsification stability. The acidified milk is milk acidified by addition of an acid, fermented milk, or acidified milk containing any of the milk acidified by addition of an acid and the fermented milk. The acidified milk contains EPA and/or DHA as a fish oil, preferably a purified fish oil or a fish oil containing EPA and/or DHA in adjusted amount. The acidified milk is produced through an emulsification process. Preferably, the emulsification is performed after a fermentation process of the acidified milk process through a two-stage emulsification process. A food product containing the acidified milk of the invention is also provided.

9 Claims, 3 Drawing Sheets

EPA AND/OR DHA-CONTAINING ACIDIC MILKS

FIELD OF THE INVENTION

This application is a 371 application of International Application No. PCT/JP01/09879 filed Nov. 12, 2001.

The present invention relates to acidified milk containing EPA and/or DHA, which is superior in oxidation and emulsification stability.

The acidified milk of the present invention has oxidation and emulsification stability over 15 days at 5° C., and is stable in oxidation and emulsification over three months at −5° C. and over one month at the room temperature.

BACKGROUND ART

Soybean milk is employed not only as materials of Tofu (bean curd), but also as beverages that are directly taken by people as functional foods in recent years. The soybean milk is usually produced as follows. First, soybeans are washed with water for removal of dust and so on. Then, the soybeans are soaked in water at the normal temperature of volume three times as much as the soybeans, and are held in the soaked condition for 5 to 20 hours depending on the season. During such a period, imbibition and germination of the soybeans occurs. Then, the imbibed soybeans are put in a grinding device, such as a mixer and a mortar, and are ground at the normal temperature while water at the normal temperature is added in volume about 5 to 6 times as much as the soybeans. Raw soybean juice (or soybean juice) is thereby produced. After heating the raw soybean juice for about 3 to 15 minutes, it is subjected to a solid-liquid separation process at high temperatures using a solid-liquid separation device, such as a centrifugal separator and a filter press. As a result, soybean milk and bean curd lees are obtained.

The soybean milk thus produced is provided as Tofu after being added with a coagulant, e.g., bittern, gluconolactone and calcium sulfate, or as beverages after being directly packed in a container and then sealed off. However, beverages containing soybean milk have unpleasant tastes, such as green grass smell and a bitter taste, due to the presence of small amounts of ill-smelling components including 2-hexenal and several kinds of saponins, and those unpleasant tastes have hitherto invited the biggest difficulty in utilization of the soybean milk. Various proposals on lactic bacteria fermentation using lactic bacteria have been made for a taste improvement of the soybean milk. But those proposals for masking the unpleasant odor of a soy bean cancel a body taste and Umami (savory taste) specific to the soy bean. Therefore, the problem of the unpleasant odor and taste specific to the soy bean is not yet overcome at the present.

It is known that soybean protein has an effect of reducing cholesterol. That fact has increased the number of people eating Tofu recently. However, containers, sauces and spices are required when eating Tofu, and places where people can eat Tofu are limited. On the other hand, when beverages containing soybean milk are packed in containers and sealed off in a portable way, there are no limitations on places for people to drink the packed beverages and people can easily take in the soybean milk as functional foods anywhere.

Meanwhile, with recent widespread diffusion of preventive medicine knowledge, it has become a prevailing practice for an increasing number of people to preventively take natural origin foods, which have physiological activities, in a healthy or half-healthy condition before they suffer from diseases, for the purpose of keeping themselves healthy. Among those foods, fish such as a horse mackerei, bonito, mackerei and sardine contains a small amount of effective natural compounds, i.e., polyunsaturated fatty acids represented by eicosapentaenoic acid (EPA) and docosahexaenoic acid (DHA), in the form of glycerides. Those natural compounds have lately received keen attention because useful physiological activities, such as a cerebral nerve activation action, a blood cholesterol and lipid lowering effect, and an antiallergic effect, have been found therein one after another in recent years. It has therefore been proposed to not only take those natural compounds as functional foods, but also to mix them in various foods.

EPA and DHA are typical ones of polyunsaturated fatty acids and are relatively abundantly contained in fat of fish (referred to as a "fish oil" hereinafter), such as fatty meat of a horse mackerei, salmon roe, yellow tail, mackerei, saury, eel, pilchard, rainbow trout, salmon, and saurel. EPA and DHA contained in the fish oil have physiological activity effects, such as a platelet aggregation inhibitory effect, a blood triglyceride lowering effect, and a blood VLDL and LDL cholesterol lowering effect, and hence have preventive and remedial effects for arteriosclerotic diseases. It is also known that depletion of DHA lowers the memory learning ability. While EPA and DHA have, on one side, have many physiological activity effects mentioned above, the fish oil containing EPA and DHA has, on the other side, a peculiar foul odor. Also, those polyunsaturated fatty acids are very easily oxidized because EPA has twenty carbons and five double bonds in a molecule and DHA has twenty-two carbons and six double bonds in a molecule. It is further known that the EPA and DHA generate an unpleasant odor and taste with deterioration of the specific taste.

Heretofore, various types of soybean milk products have been proposed in consideration of the state of the art described above. As one example of the prior art, Japanese Patent Laid-Open Publication No. 7-255406 discloses a method of producing soy bean processed food enriched with polyunsaturated fat, wherein soybean milk containing polyunsaturated fat is produced by mixing soybean milk and about 1% to about 25% of polyunsaturated fat with respect to the weight of soybean protein in the soybean milk. According to the detailed description in the Publication, "a maximum amount of EPA(DHA)-containing liquid fat uniformly dispersible in 18 liters of soybean milk (about 650 g of protein content) is 160 g (about 25% with respect to the weight of protein in the soybean milk)", and "if the fat content exceeds about 25%, the fat is not uniformly dispersed and an oil component is separated".

As another example of the prior art, Japanese Patent Laid-Open Publication No. 10-42819 discloses "a method of producing a beverage containing DHA-mixed soybean milk, the method comprising the steps of adding and mixing soybean milk and a DHA-containing fish oil at a weight ratio of 1:0.2 to 1, thereby preparing an emulsion of the DHA-containing fish oil, and further diluting the emulsion with the soybean milk".

Further, Japanese Patent Laid-Open Publication No. 6-90662 discloses "a method of producing fermented milk wherein, when producing fermented milk containing DHA and EPA, DHA and EPA are mixed in raw milk which is then subjected to lactic bacterial fermentation, or DHA and EPA are mixed in fermented milk which has been subjected to lactic bacterial fermentation".

DISCLOSURE OF THE INVENTION

An object of the present invention is to provide a dairy product, particularly acidified milk, containing fish-oil-originated EPA and/or DHA, which is superior in oxidation and emulsification stability.

The present invention is intended to achieve the above object and resides in acidified milk containing EPA and/or DHA wherein the acidified milk has oxidation and emulsification stability, and the acidified milk is milk acidified by addition of an acid, fermented milk, or acidified milk containing any of the milk acidified by addition of an acid and the fermented milk. Therefore the present invention resides in acidified milk containing EPA and/or DHA wherein the acidified milk has oxidation and emulsification stability, wherein the acidified milk is milk acidified by addition of an acid, fermented milk, or acidified milk containing any of the milk acidified by addition of an acid and the fermented milk.

The acidified milk contains EPA and/or DHA as a fish oil or preferably a purified fish oil. In this case, the present invention resides in acidified milk containing EPA and/or DHA wherein the acidified milk has oxidation and emulsification stability, the acidified milk being milk acidified by addition of an acid, fermented milk, or acidified milk containing any of the milk acidified by addition of an acid and the fermented milk, EPA and/or DHA being contained as a fish oil or preferably a purified fish oil.

The fish oil contains EPA and/or DHA in adjusted amount. In this case, the present invention resides in acidified milk containing EPA and/or DHA wherein the acidified milk has oxidation and emulsification stability, the acidified milk being milk acidified by addition of an acid, fermented milk, or acidified milk containing any of the milk acidified by addition of an acid and the fermented milk, EPA and/or DHA being contained in adjusted amount as a fish oil or preferably a purified fish oil.

The acidified milk is produced through an emulsification process, which is preferably a two-stage emulsification process and performed after a fermentation process of the acidified milk. In this case, the present invention resides in acidified milk containing EPA and/or DHA wherein the acidified milk has oxidation and emulsification stability, the acidified milk being milk acidified by addition of an acid, fermented milk, or acidified milk containing any of the milk acidified by addition of an acid and the fermented milk, EPA and/or DHA being contained in adjusted amount as a fish oil or preferably a purified fish oil, the acidified milk being produced through an emulsification process, which is preferably a two-stage emulsification process and performed after a fermentation process of the acidified milk.

Also, the present invention resides in a food product containing acidified milk which contains EPA and/or DHA and has oxidation and emulsification stability, and the acidified milk being contained in the food product is milk acidified by addition of an acid, fermented milk, or acidified milk containing any of the milk acidified by addition of an acid and the fermented milk. Therefore the present invention resides in a food product containing acidified milk which contains EPA and/or DHA and has oxidation and emulsification stability, wherein the acidified milk is milk acidified by addition of an acid, fermented milk, or acidified milk containing any of the milk acidified by addition of an acid and the fermented milk.

In the food product, the acidified milk contains EPA and/or DHA as a fish oil or preferably a purified fish oil. In this case, the present invention resides in a food product containing acidified milk which contains EPA and/or DHA and has oxidation and emulsification stability, the acidified milk being milk acidified by addition of an acid, fermented milk, or acidified milk containing any of the milk acidified by addition of an acid and the fermented milk, EPA and/or DHA being contained as a fish oil or preferably a purified fish oil.

In the food product, the fish oil contains EPA and/or DHA in adjusted amount. In this case, the present invention resides in a food product containing acidified milk which contains EPA and/or DHA and has oxidation and emulsification stability, the acidified milk being milk acidified by addition of an acid, fermented milk, or acidified milk containing any of the milk acidified by addition of an acid and the fermented milk, EPA and/or DHA being contained in adjusted amount as a fish oil or preferably a purified fish oil.

In the food product, the acidified milk is produced through an emulsification process, which is preferably a two-stage emulsification process and performed after a fermentation process of the acidified milk. In this case, the present invention resides in a food product containing acidified milk which contains EPA and/or DHA and has oxidation and emulsification stability, the acidified milk being milk acidified by addition of an acid, fermented milk, or acidified milk containing any of the milk acidified by addition of an acid and the fermented milk, EPA and/or DHA being contained in adjusted amount as a fish oil or preferably a purified fish oil, the acidified milk being produced through an emulsification process, which is preferably a two-stage emulsification process and performed after a fermentation process of the acidified milk.

DETAILED DESCRIPTION OF THE INVENTION

Figure 1:
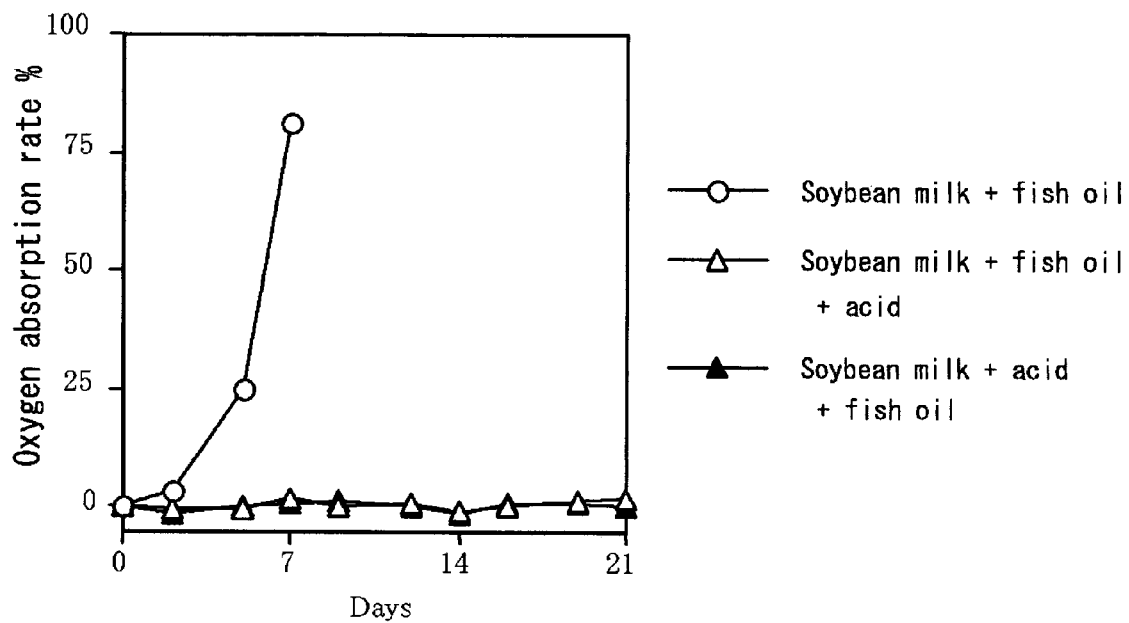
FIG. 1 is a graph for explaining oxidation stability of acidified milk.

Acidified milk of the present invention means a variety of products including ones obtained by acidifying milk, soybean milk, or the like, and others which are acidified by addition of an acid such as lactate, gluconic acid and citric acid. The pH value is generally preferably not higher than about 4.5, but it can be optionally selected depending on the types of foods to be produced and preference of tastes.

Soybean milk, preferably soybean milk containing 3% or more of soybean solid part, for use in the present invention may be obtained by any suitable method, and it can be, for example, soybean milk produced by a usual method from soybeans and/or defatted soybeans. Preferably, skin- and albumen-removed soybeans are used in point of providing soybean milk with a better taste. The soybean milk thus produced is provided as a beverage containing the soybean milk as it is, or Tofu after being added with a coagulant, e.g., bittern, gluconolactone and calcium sulfate, or fermented soybean milk (acidified soybean milk) after being subjected to lactic bacteria fermentation. Thus, the soybean milk is any one selected from among adjusted soybean milk, a beverage containing soybean milk, acidified soybean milk, and Tofu obtained by curding soybean milk.

Soybean milk can be produced by grinding whole soybeans and/or skin-removed soybeans, which are in a hydrated condition after or without being soaked in water, to obtain soybean juice, and then by removing insoluble fractions from the soybean juice through, e.g., filtration. More specifically, soybean milk is produced as follows. First, whole soybeans, skin-removed soybeans, and/or skin- and albumen-removed soybeans are contacted with warm or hot water at 50 to 100° C. to remove components which are soluble in the warm or hot water. Then, the imbibed soybeans are ground to obtain raw soybean juice (or soybean juice). The soybean juice is immediately introduced to a solid-liquid separation device, such as a centrifugal separator, for quick separation into solid and liquid parts. A filtrate (soybean milk) obtained after removing an insoluble fraction (solid part called bean curd lees) is preferably used as the soybean milk in the present invention. For grinding the imbibed soybeans, an ordinary grinding device, such as a mortar, a mixing machine and a mixer, can be used. The obtained soybean milk may be subjected to heat sterilization at 135 to 150° C. for 1 to 120 seconds, and then cooled.

In the case of fermenting soybean milk with lactic bacteria, the soybean milk can be produced by a usual method from soybeans and/or defatted soybeans, but may preferably contain 1.0 weight % or less of soluble glucose in a dry material of the soybean milk for the purpose of facilitating control of the lactic bacteria fermentation and providing a product having a fine fresh taste free from unfavorable tastes. Lactic bacteria assimilation saccharides (e.g., oligosaccharides) are not always required, but addition of those saccharides promotes the lactic bacteria fermentation and provides soybean milk having a better taste through the lactic bacteria fermentation. Lactic bacteria for use in the lactic bacteria fermentation are not limited to particular ones, but may be strains usually employed in yogurt, or may be any of combinations of known strains used for improving the taste of the soybean milk. For example, known strains of lactic bacteria belonging to such genuses as *Lactobacillus bulgaricus, Lactobacillus acidophilus, Lactobacillus casei, Streptococcus thermophilus, Streptococcus thermophilus, Streptococcus lactis*, and Bifidobacterium, are usable. Those lactic bacteria can be used either alone or a combination of two or more selected from among them.

A fermentation method can be implemented by adding a bulk starter prepared in advance, or by adding frozen concentrated bacteria or freeze-dry concentrated bacteria directly in the soybean milk. Though depending on the temperature and time of a fermentation process, the amount of added bulk start is, e.g., 0.5 to 15%, and in the case of directly adding lactic bacteria, the amount of the added lactic bacteria is selected so that the onset bacteria density is, e.g., not less than $10^5$/ml.

The lactic bacteria fermentation can be performed at the fermentation temperature of 20 to 50° C. for 3 to 48 hours and preferably 25 to 45° C. for 4 to 24 hours.

A fermentation device may be a similar one as that usually employed for producing fermented milk using milk as materials.

The fish oil for use in the present invention is a purified fish oil and preferably a purified fish oil containing 28% or more of EPA. Also, The fish oil may be added with 0.5% or more of tocopherol as an antioxidant. The purified fish oil is produced through a first purification process (degumming→refining with alkali→bleaching→filtration) in which a fish oil from raw material fish, such as sardine, is processed to obtain a raw fish oil, and a second purification process (adsorption→distillation→deodorization→addition of antioxidant) in which the raw fish oil is processed into the purified fish oil. By carrying out a wintering process in addition to the usual purification process, it is possible to increase the content of polyunsaturated fatty acids such as EPA and DHA.

A method of producing fish-oil-originated EPA/DHA in acidified milk comprises steps of preparing acidified milk through a series of steps, degassing the prepared acidified milk, and then mixing a fish oil in it. In a subsequent emulsifying process, to prevent the acidified milk from taking in oxygen, the emulsification is carried out under an atmosphere replaced by nitrogen, or using a mixing device of the type not allowing the soybean milk to take in air. The emulsification is preferably performed in two stages. Following the first stage of rough emulsification, the second stage of fine emulsification is performed immediately without a time lag. After the emulsification process, the soybean milk containing the fish oil is subjected to heat sterilization and packed in a container with a packing machine.

The acidified milk of the present invention includes various types of products made of soybean milk as a main material. The soybean milk includes, for example, raw soybean milk, adjusted soybean milk obtained by processing raw soybean milk, and beverages containing soybean milk.

A food product containing the acidified milk of the present invention implies foods that are made of acidified milk so far, foods that can be partly replaced by acidified milk without problems, and foods to which acidified milk can be added without problems. By using the acidified milk of the present invention in the process of producing those foods, the fish oil containing EPA/DHA can be easily mixed in the foods. The foods that can be partly replaced by acidified milk include, for example, dairy products such as milk, yogurt, cheese and butter, lactic bacteria drinks, and emulsion products such as margarine and spread. The foods to which acidified milk can be added include, for example, breads, cakes, pastes, and sauces.

It has proved through experiments that a proper combination of protein contained in milk and acidity is effective in achieving oxidation and emulsification stability of EPA/DHA in the acidified milk.

EXAMPLES

The present invention will be described below in more detail in connection with Examples. Note that the present invention is not limited to the following Examples.

Fat used in Examples is a purified fish oil made by Nippon Suisan Kaish Ltd. and has physical properties shown in Table 1 given below. This purified fish oil is produced through a first purification process (degumming→refining with alkali→bleaching→filtration) in which a fish oil from raw material fish, such as sardine, is processed to obtain a raw fish oil), a wintering process of the raw fish oil, and a second purification process (adsorption→distillation→deodorization→addition of antioxidant) in which the raw fish oil is processed into the purified fish oil.

TABLE 1

| Item | Standards | Analyzing method |
| --- | --- | --- |
| Properties | Pale yellow liquid with no significant unpleasant odor | Visual observation and sensuality evaluation |

TABLE 1-continued

| Item | Standards | Analyzing method |
|---|---|---|
| Fatty acid composition | | Gas chromatograph |
| EPA | 28.0% or more | |
| DHA | 12.0% or more | |
| Acid value | 1.00 or less | Fat analysis method |
| Peroxide value | 5.0 meq/kg or less | Fat analysis method |

Example 1

Evaluation of Oxidation Stability

<Production Method>

A sample for evaluation was obtained by dropping an EPA-containing fish oil into soybean milk, or soybean milk mixed with solutions of gluconic acid and lactate, and performing an emulsification process of the soybean milk as described below.

Soybean milk used: non-processed soybean milk "Fuji-sunny" made by Fuji Oil K.K. (4.9% of protein and 3.0% of fat part)

Fat used: purified fish oil (Type 2) made by Nippon Suisan KAISHA LTD.

Production method: An acid (50% of gluconic acid solution: 0.8% and 50% of lactate solution: 0.55%) was added to soybean milk. The soybean milk was then diluted with distilled water so that the soybean milk concentration was 42.5%. The diluted soybean milk was subjected to pre-emulsification at 8,000 rpm for 2 minutes using TK HOMO MIXER (made by Tokushu Kika K.K.) while dropping an EPA-containing fish oil. An emulsion was then obtained after sonication (120 w) for 10 minutes. Another emulsion was also obtained in a similar manner just by changing the order at which the acid is added. Specifically, another emulsion was prepared by adding the same acid to soybean milk into which an EPA-containing fish oil has already been dropped, and emulsifying the soybean milk containing the acid again.

<Evaluation Method>

Each 10 ml of the above-mentioned samples was put in a gas chromatograph vial with a capacity of 30 ml, and then measured for the oxygen concentration in a head space of the vial by a gas chromatograph while keeping temperature at 5° C. Further, a sample containing only the soybean milk and the acid with no addition of any fat was put in the gas chromatograph vial, and then measured for the oxygen concentration in the head space of the vial likewise while keeping temperature at 5° C. According to the following equations, that measured value of the sample blank was subtracted from the above measured value of the sample to obtain the oxygen absorption rate of the fish oil, and the oxygen absorption rate was calculated based on the oxygen amount in the head space for each sample. Calculated results are shown in FIG. 1.

(oxygen absorption rate of sample)−(oxygen absorption rate of sample blank)=(oxygen absorption rate of fish oil)

(oxygen absorption rate (%))=(oxygen absorption rate of fish oil)×100/(oxygen amount in head space)

<Results>

1. Evaluation of Oxidation Stability

As shown in FIG. 1, it was apparent that the sample containing the soybean milk and the acid was much more effective in suppressing the oxygen absorption amount than the sample containing the soybean milk alone, and exhibited much better results.

2. Evaluation of Emulsification Stability

Emulsification stability was evaluated by visually observing an change in the state of emulsification of each sample. Observed results are shown in Table 2 given below.

Figure 2:
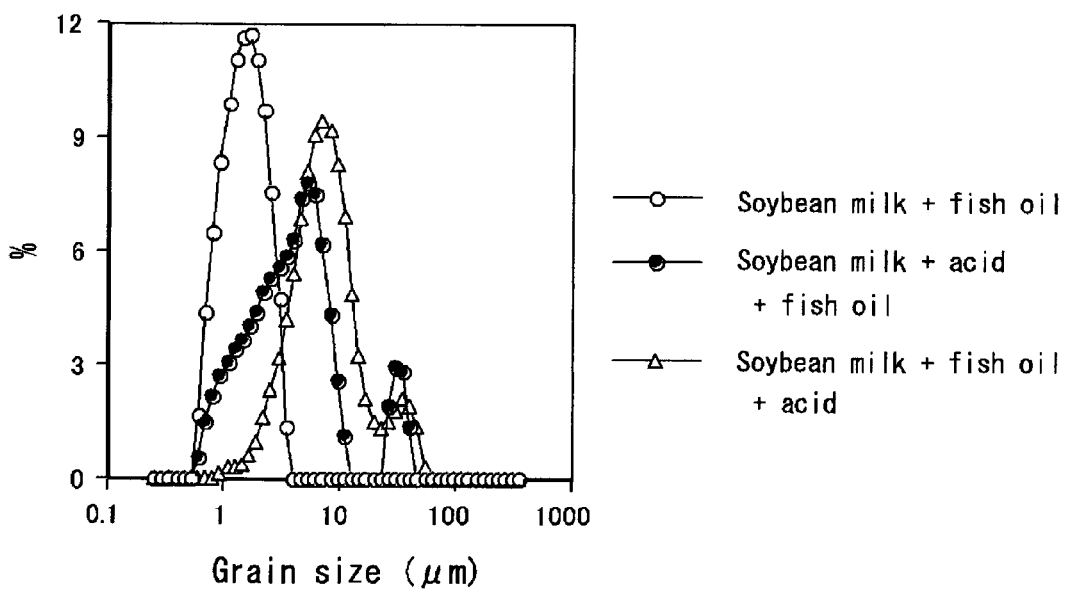
FIG. 2 is a graph for explaining an influence caused upon emulsification stability by the order at which an acid is added in a production process.

For emulsification stability, satisfactory results were obtained in all of the samples. The grain size distribution of each sample immediately after the preparation is shown in FIG. 2, and mean±standard deviation of the grain size is listed for each sample in Table 3 given below.

The sample containing the soybean milk and the acid had a tendency to increase the mean grain size to some extent. In all of the samples, however, the mean grain size was on the order of several microns, and neither aggregation nor precipitation were observed during a period of preservation.

TABLE 2

| | State of emulsification | | | | |
|---|---|---|---|---|---|
| | Sample/Preservation days | | | | |
| | 2 | 5 | 7 | 14 | 21 |
| Soybean milk + fish oil | G | G | G | G | C |
| Soybean milk + acid + fish oil | G | G | G | G | G, C |
| Soybean milk + fish oil + acid | G | G | G | G | G |

State of emulsification
G: good,
C: creaming, and
AP: aggregation and/or precipitation

TABLE 3

| Mean ± Standard Deviation | |
|---|---|
| Soybean milk + fish oil: | 1.34 ± 0.18 |
| Soybean milk + acid + fish oil: | 4.87 ± 0.41 |
| Soybean milk + fish oil + acid: | 6.51 ± 0.32 |

Example 2

Evaluation of Oxidation Stability

<Production Method>

Samples for evaluation were obtained by dropping an EPA-containing fish oil into various kinds of protein solutions.

Protein solutions used include soybean milk (non-processed soybean milk "Fuji-sunny" made by Fuji Oil K.K., 9.1% of solid part, 4.9% of protein, 3.0% of fat part, 0.9% of carbohydroxide, and 0.3% of ash); fermented soybean milk (fermented soybean milk "Fuji-sunny" made by Fuji Oil K.K., 12.5% of solid part, 4.0% of protein, 2.4% of fat part, 5.7% of carbohydroxide, and 0.4% of ash); milk (component non-processed 3.6 milk made by Meiji Milk Products K.K., 3.1% of protein, 3.7% of fat part, 4.9% of carbohydroxide, 8.3% of non-fat milk solid, and 3.6% of milk fat); and fermented milk (drink plain yogurt made by Tohoku Kyodo Milk Products K.K., 3.05% of protein, 3.15% of fat part, 4.55% of carbohydroxide, 8% of non-fat milk solid, and 3% of milk fat). Also, the purified fish oil used was DD Oil Type 2 made by Nippon Suisan KAISHA LTD., which contained 28% of EPA and 12% of DHA.

Production method: Each of the protein solutions was diluted with distilled water so that the protein content was 1.7%. The diluted protein solutions was subjected to pre-emulsification at 8,000 rpm for 2 minutes using TK HOMO MIXER (made by Tokushu Kika K.K.) while dropping an EPA-containing fish oil. An emulsion was then obtained after sonication (120 w) for 10 minutes.

<Evaluation Method>

Figure 3:
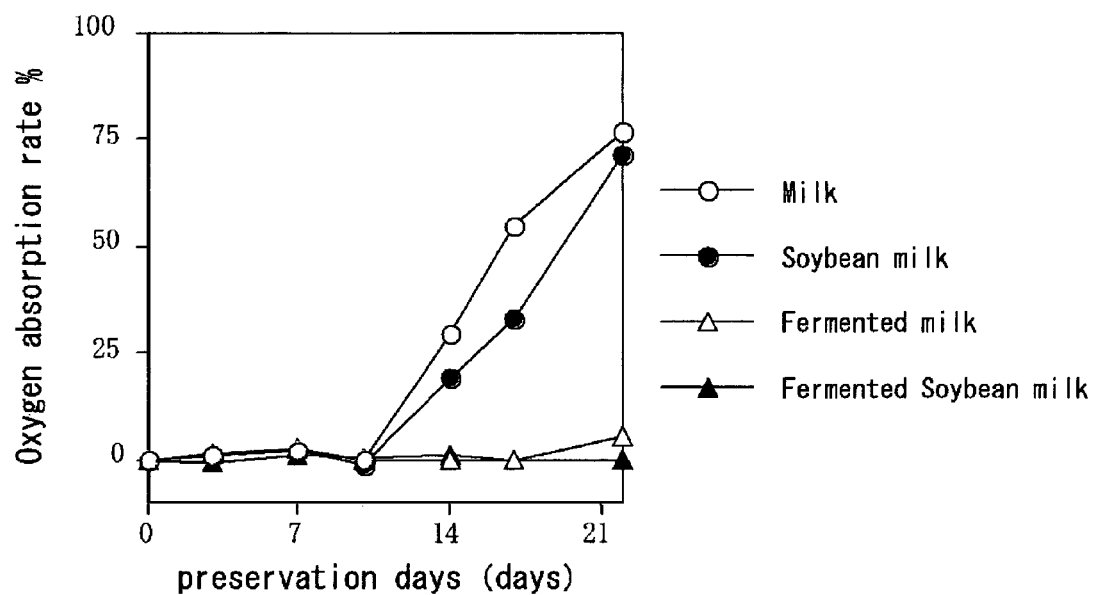
FIG. 3 is a graph for explaining oxidation stability of fermented soybean milk, fermented milk, soybean milk, and milk.

Each 10 ml of the above-mentioned samples was put in a gas chromatograph vial with a capacity of 30 ml, and then measured for the oxygen concentration in a head space of the vial by a gas chromatograph while keeping temperature at 5° C. Further, a sample containing only the protein solutions with no addition of any fat was put in the gas chromatograph vial, and then measured for the oxygen concentration in the head space of the vial likewise while keeping temperature at 5° C. According to the following equations, that measured value of the sample blank was subtracted from the above measured value of the sample to obtain the oxygen absorption rate of the fish oil, and the oxygen absorption rate was calculated based on the oxygen amount in the head space for each sample. Calculated results are shown in FIG. 3.

(oxygen absorption rate of sample)−(oxygen absorption rate of sample blank)=(oxygen absorption rate of fish oil)

(oxygen absorption rate (%))=(oxygen absorption rate of fish oil)×100/(oxygen amount in head space)

<Results>

1. Evaluation of Oxidation Stability

As shown in FIG. 3, the oxidation stability was held in a more satisfactory state in the order of fermented soybean milk≧fermented milk>soybean milk>milk. Apparently, the fermented soybean milk and the fermented milk were more effective in suppressing the oxygen absorption amount than the usual milk and soybean milk, and exhibited better results. Among them, in particular, the fermented soybean milk exhibited the most factory result.

2. Evaluation of Emulsification Stability

Emulsification stability was evaluated for the fermented soybean milk and the fermented milk, which are superior in oxidation stability, by visually observing an change in the state of emulsification of each sample. Observed results are shown in Table 4 given below.

More satisfactory emulsification stability was obtained in the order of the fermented soybean milk>>the fermented milk. Thus, the fermented soybean milk was superior to the fermented milk in point of emulsification stability.

Figure 4:
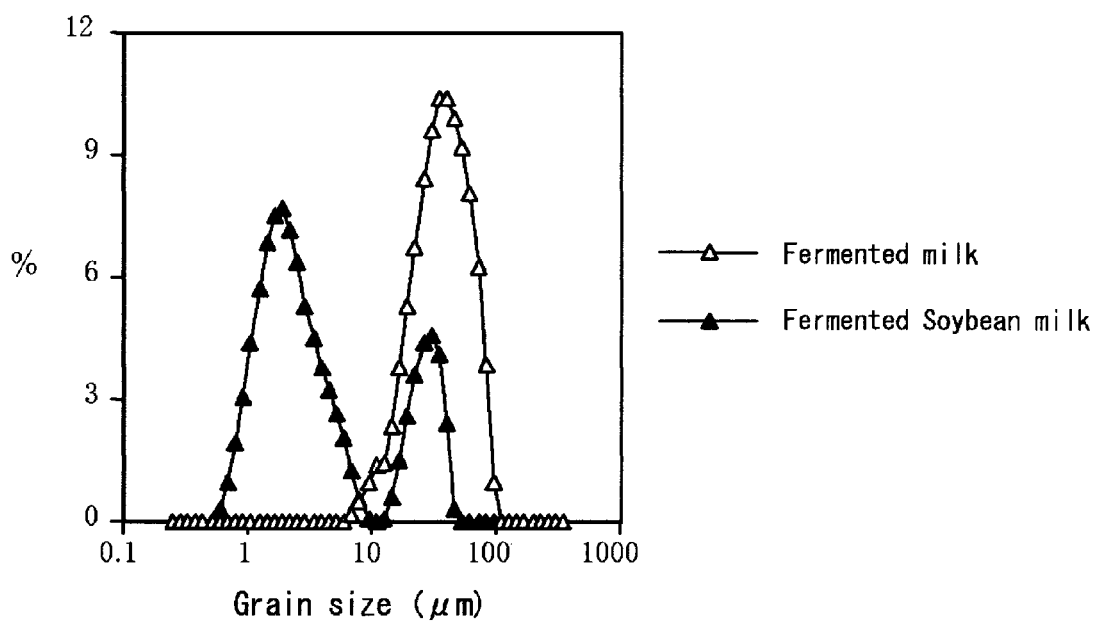
FIG. 4 is a graph for explaining emulsification stability of fermented soybean milk and fermented milk.

The grain size distribution of each sample immediately after the preparation is shown in FIG. 4, and mean±standard deviation of the grain size is listed for each sample in Table 5 given below.

For the fermented milk, the mean grain size was relatively large, and aggregation occurred between emulsion grains and precipitation was observed during a period of preservation.

TABLE 4

| | State of emulsification | | | | |
|---|---|---|---|---|---|
| | Sample/Preservation days | | | | |
| | 3 | 7 | 14 | 17 | 22 |
| Fermented milk | G | G | C | GC | AP |
| Fermented soybean milk | G | G | G | G | GC |

State of emulsification
G: good,
C: creaming, and
AP: aggregation and precipitation

TABLE 5

| | Mean ± Standard Deviation |
|---|---|
| Fermented milk: | 32.60 ± 0.23 |
| Fermented soybean milk: | 3.63 ± 0.52 |

Example 3

Clinical Test on Healthy Volunteers

<Sample Used>

A sample used was fermented soybean milk (one 125-ml bottle mixed with 900 mg of EPA and 350 mg of DHA) in which a purified fish oil containing eicosapentaenoic acid and docosahexaenoic acid (referred to as "EPA•DHA" hereinafter). The nutrient composition and material combination ratio of the used sample are listed in Tables 6 and 7 given below. The fermented soybean milk was a commercialized one made by Fuji Oil K.K., and the purified fish oil containing EPA•DHA was a commercialized one made by Nippon Suisan Kaisha Ltd.

<Subjects>

Eleven volunteers (mean age of 41.9±8.5, male) were selected who had serum triglycride values of not less than 150 mg/dl and serum whole cholesterol values of not less than 200 mg/dl, and were living in healthy conditions.

<Test Method>

Each of the volunteers continued drinking one bottle of a beverage mixed with the purified fish oil containing EPA•DHA (one 125-ml bottle mixed with 900 mg of EPA and 350 mg of DHA) per day for three months. After about 12 weeks from starting to take in the beverage, a change of serum fat was measured.

<Results>

Figure 5:
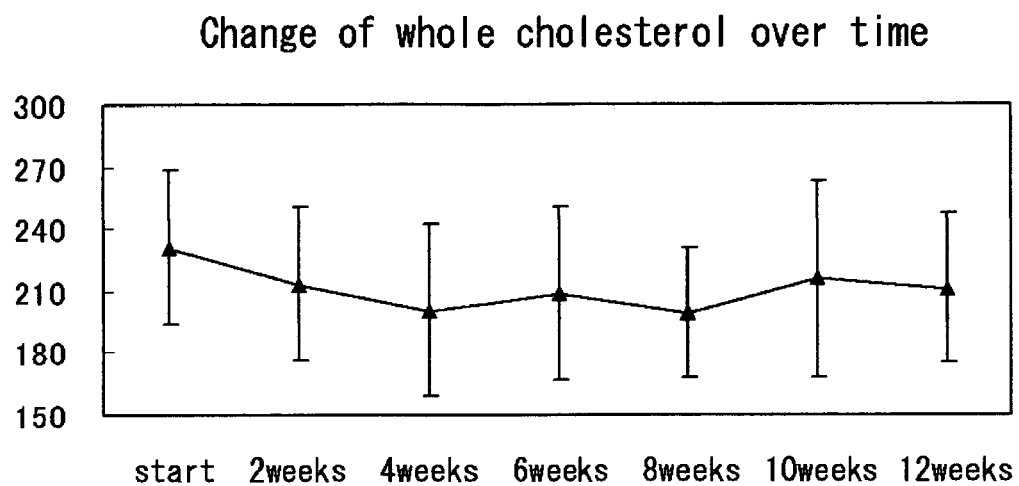
FIG. 5 is a graph showing a change of whole cholesterol over time resulting from a test in Example 3.
Figure 6:
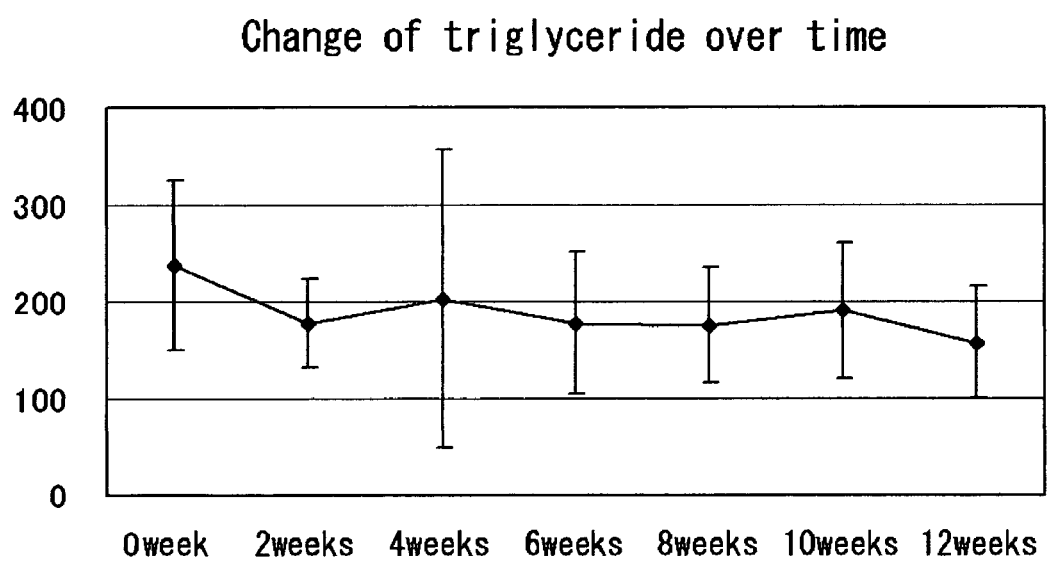
FIG. 6 is a graph showing a change of triglyceride over time resulting from the test in Example 3.

The serum whole cholesterol value was reduced from 231±31 mg/dl (mean±standard deviation, this similarly applied to values given below) at the time of starting to take in the beverage down to 211±36.4 mg/dl, i.e., 8.7%, after 12 weeks (FIG. 5). Also, the serum triglycride value was reduced from 236.8±88.2 mg/dl at the time of starting to take in the beverage down to 156.8±56.4 mg/dl, i.e., 33.8%, after 12 weeks (FIG. 6). During the test period, neither problematic side effects nor drop-out examples occurred. It was hence confirmed from those results that the fermented soybean milk containing EPA are foods which people are able to drink continuously and which are useful for health care of persons having relatively high serum fat values.

TABLE 6

Nutrient Composition of Tested Food Product

| Analysis item | Unit | |
|---|---|---|
| Water | g | 108.3 |
| Protein | g | 2.0 |
| Fat | g | 5.1 |
| Ash | g | 0.1 |
| Carbohydrate | g | 0.1 |
| Energy | kcal | 79.3 |
| Sodium | mg | 21.0 |
| Eicosapentaenoic acid (EPA) | g | 0.84 |
| Docosahexaenoic acid (DHA) | g | 0.35 |

TABLE 7

Combination Ratio of Materials

| Materials | Composition ratio |
|---|---|
| Fermented soybean milk | 42.4% |
| Purified fish oil containing EPA · DHA | 2.6% |
| Other sweetener, flavor, etc. | 4.4% |
| Water | 50.5% |

Example 4

A preservability test was conducted on two samples of fermented soybean milk which were each obtained using the same purified fish oil and fermented soybean milk as those used in Example 3, and which contained 1.71% and 2.57% of purified fish oil, respectively, as well as on a control sample containing only fermented soybean milk added with no fish oil. Each of the samples was preserved in a condition being packed in an aluminum-coated brick pack.

Evaluation was made in four-stage ratings for fat separation, five-stage ratings for precipitation, and four-stage ratings for the occurrence of fish odor.

<Ratings for Fat Separation>
1: no separation of oil component
2: creaming (−: a part of the liquid surface becomes cloudy, ±: a half of the liquid surface becomes cloudy, +: most of the liquid surface becomes cloudy, and ++: the whole of the liquid surface becomes cloudy)
3: fat separation <Ratings for Precipitation>
1: no precipitation
2: precipitation in a part of the bottom surface
3: a half of the bottom surface covered
4: most of the bottom surface covered
5: the whole of the bottom surface covered
( ): (+) no dispersion occurred even upon shaking <Ratings for Occurrence of Fish Odor>
1: no fish odor perceived
2: fish odor slight perceived (at such a level as not perceived by smelling, but perceivable upon drinking)
3: fish odor perceived (at such a level that a fish odor is perceived when people smell intentionally)
4: fish odor apparent perceived (at such a level that a fish odor is apparently smelt and people feel unpleasant)

The grain size was measured on the median diameter using a laser grain size analyzer made by Horiba Mfg. K.K.

Evaluated and measured results are listed in Tables 8, 9 and 10 given below.

In each Table, one month in an accelerated test (preservation at 35° C.) corresponds to about three months at the room temperature (25° C.).

As a result of the accelerated test, no fat separation was found and just a slight concentration gradient occurred.

The level 2 in the occurrence of fish odor represents a level allowable as commercial goods.

TABLE 8

Fermented Soybean Milk Added with No Fish Oil

| Preservation period | Just after production | After preservation for 1 month | | |
|---|---|---|---|---|
| Preservation temperature | — | 5° C. | 20° C. | 35° C. |
| Solid part (%) | 8.92 | 8.88 | 8.88 | 8.91 |
| pH (15° C.) | 3.69 | 3.66 | 3.69 | 3.69 |
| Grain size change (μm) | — | 0.09 | 0.3 | 0.18 |
| Oil layer separation | 1 | 1 | 1 | 1 |
| Precipitation | 1 | 2 | 2 | 2 |
| Color tone L | 86.1 | 86.18 | 86.09 | 86.02 |
| a | −1.36 | −1.13 | −1.01 | −1.01 |
| b | 10.56 | 10.35 | 10.19 | 10.99 |
| ΔE (just after production) | — | 0.32 | 0.51 | 0.56 |

TABLE 9

Fermented Soybean Milk Added with 1.7% of Fish Oil

| Preservation period | Just after production | After preservation for 1 month | | |
|---|---|---|---|---|
| Preservation temperature | — | 5° C. | 20° C. | 35° C. |
| Solid part (%) | 10.8 | 10.71 | 10.71 | 10.71 |
| pH (15° C.) | 3.7 | 3.69 | 3.72 | 3.72 |
| Grain size change (μm) | — | −0.49 | −0.27 | −0.84 |
| Oil layer separation | 1 | 2(±) | 2(±) | 2(±) |
| Precipitation | 1 | 2 | 4 | 5 |
| Color tone L | 88.51 | 88.56 | 88.47 | 88.36 |
| a | −1.1 | −1.03 | −0.95 | −1.03 |
| b | 9.51 | 9.61 | 9.88 | 10.78 |
| ΔE (just after production) | — | 0.13 | 0.4 | 1.28 |
| Occurrence of fish odor | 1 | 1 | 1 | 2 |

TABLE 10

Fermented Soybean Milk Added with 2.57% of Fish Oil

| Preservation period | Just after production | After preservation for 1 month | | |
|---|---|---|---|---|
| Preservation temperature | — | 5° C. | 20° C. | 35° C. |
| Solid part (%) | 11.92 | 11.88 | 11.88 | 11.88 |
| pH (15° C.) | 3.72 | 3.69 | 3.72 | 3.73 |
| Grain size change (μm) | — | 0.69 | 0.61 | 0.52 |
| Oil layer separation | 1 | 2(±) | 2(±) | 2(±) |
| Precipitation | 1 | 4 | 5(+) | 5(+) |
| Color tone L | 88.76 | 88.82 | 88.72 | 88.57 |
| a | −1.11 | −1.02 | −0.93 | −0.96 |
| b | 9.46 | 9.62 | 9.94 | 10.81 |
| ΔE (just after production) | — | 0.19 | 0.51 | 1.37 |

TABLE 10-continued

Fermented Soybean Milk Added with 2.57% of Fish Oil

| Preservation period | Just after production | | After preservation for 1 month | |
|---|---|---|---|---|
| Occurrence of fish odor | 2 | 2 | 2 | 3 |

INDUSTRIAL APPLICABILITY

According to the present invention, acidified milk containing EPA•DHA can be provided which has oxidation and emulsification stability, which does not cause a fish odor originating from a fish oil used as materials, which is superior in taste, smell and texture, which shows good preservability of EPA•DHA, and which enables people to take in EPA•DHA together with acidified milk as a good protein source.

Also, according to the present invention, acidified milk containing EPA•DHA can be provided, which is produced by adding a required amount fat (fish oil) to acidified milk through an emulsification process without exposing the fish oil to oxygen, and hence which has oxidation and emulsification stability.

The invention claimed is:

1. An acidified soybean milk mixture uncoagulated and in liquid form, comprising:
soybean milk;
acid to acidify the mixture to pH 4.5 or less; and
eicosapentaenoic acid (EPA) and/or docosahexaenoic acid (DHA),
wherein the acidified milk mixture has oxidation and emulsification stability over 15 days at 5° C., and wherein the EPA and/or DHA is added as a purified fish oil which has acid value of 1.00 or less and peroxide value of 5.0 meq/kg or less.

2. The acidified soybean milk mixture according to claim 1, wherein said fish oil has content of EPA and/or DHA higher than that of raw fish oil.

3. The acidified soybean milk mixture according to any one of claims 1 and 2, wherein the acidified soybean milk is emulsified through an emulsification process performed on the acidified milk during or after the addition of the EPA and/or DHA to the acidified milk.

4. The acidified soybean milk mixture according to claim 3, wherein the emulsification process is a two-stage emulsification process.

5. The acidified soybean milk mixture according to any one of claims 1 and 2, wherein the mixture is contained in a beverage.

6. The acidified soybean milk mixture according to any one of claims 1 and 2, wherein said fish oil contains 28% or more of EPA.

7. The acidified soybean milk mixture of claim 1, wherein the mixture is contained in a beverage or food to be administered to a person in need of reducing serum fat levels.

8. An acidified soybean milk mixture, comprising:
soybean milk;
acid to acidify the mixture to pH 4.5 or less; and
eicosapentaenoic acid (EPA) and/or docosahexaenoic acid (DHA),
wherein the acidified soybean milk has oxidation and emulsification stability over 1 month at 20° C.

9. An acidified soybean milk mixture, comprising:
soybean milk;
acid to acidify the mixture to pH 4.5 or less; and
eicosapentaenoic acid (EPA) and/or docosahexaenoic acid (DHA),
wherein the acidified soybean milk has oxidation and emulsification stability over 1 month at 35° C.

* * * * *